United States Patent [19]

Fabinski et al.

[11] 4,306,153

[45] Dec. 15, 1981

[54] NONDISPERSIVE INFRARED GAS ANALYZER

[75] Inventors: Walter Fabinski, Kriftel; Margareta Ascherfeld, Oberursel, both of Fed. Rep. of Germany

[73] Assignee: Hartmann & Braun Aktiengesellschaft, Frankfurt, Fed. Rep. of Germany

[21] Appl. No.: 129,691

[22] Filed: Mar. 12, 1980

[30] Foreign Application Priority Data

Mar. 15, 1979 [DE] Fed. Rep. of Germany ....... 2910188

[51] Int. Cl.³ ............................................ G01N 21/26
[52] U.S. Cl. .................................... 250/344; 250/345
[58] Field of Search ...................... 250/343, 344, 345; 356/436, 437; 422/83

[56] References Cited

U.S. PATENT DOCUMENTS

| | | | |
|---|---|---|---|
| 2,844,066 | 7/1958 | Friel | 250/345 X |
| 2,898,800 | 8/1959 | Bergson | 250/344 X |
| 2,951,939 | 9/1960 | Luft | 250/344 |
| 3,725,702 | 4/1973 | Schaefer | 250/343 |
| 3,925,667 | 12/1975 | Staab | 250/343 |
| 3,953,734 | 4/1976 | Dimeff | 250/344 X |
| 4,156,812 | 5/1979 | Staab | 250/345 |

Primary Examiner—Davis L. Willis
Attorney, Agent, or Firm—Smyth, Pavitt, Siegemund & Martella

[57] ABSTRACT

A two-beam, infrared gas analyzer includes a front and a rear detection cell in each path filled with gas of the type to be detected; and a pressure-differential chamber with capacitor pick-up is connected to these front and rear cells. The rear cells are constructed to ensure substantially complete absorption of all radiation of the absorption band being characteristic of the component to be detected. In one example, filters are interposed between front and rear cells for broadband, i.e., nonselective attenuation. Alternatively, the rear cells are connected to a reservoir of the same gas to attenuate pressure variations. Either case enhances frequency selectivity by reducing cross sensitivity.

9 Claims, 2 Drawing Figures

NONDISPERSIVE INFRARED GAS ANALYZER

BACKGROUND OF THE INVENTION

The present invention relates to nondispersive, infrared gas analyzers.

Gas analyzers of the type to which the invention pertains include, for example, two radiation beams and branches, synchronous modulation for both of the branches, and chambers or cells in the branches, one for the measuring gas, the other one for a reference gas. The two radiation beams are separately received, each by a two-level detector being comprised of two chambers filled essentially with gas of the type to be detected and being sequentially traversed by the respective beam. A differential pressure gauge (membrane capacitor) is connected to these detector chambers in various ways to generate a signal representing the concentration of the particular component in the measuring gas. Analyzers of this type are, for example, disclosed in U.S. Pat. Nos. 3,725,702 and 4,156,812 and German Pat. No. 1,302,592.

Analyzers operating on the basis of frequency-selective absorption of radiation by the component to be detected produce measuring errors if any other gas in the system has an absorption band or line that overlaps any band or line of the component of interest. Obviously, the error will be the more pronounced, the lower the concentration of the desired component and the higher the concentration of the other gas. If that interference gas is present at exactly fixed amounts and concentrations, it can readily be eliminated during nulling of the instrument. The situation is different if the interfering component varies in concentration.

The problem, also called "cross sensitivity", has been recognized and dealt with in various ways; see, for example, U.S. Pat. No. 3,925,667 and German Pat. No. 27,02,744. The U.S. Pat. No. 3,925,667, in particular, deviates from the overall layout, as described, in that both beams traverse the measuring gas equally; and the detector portion for one beam has but one detection chamber.

It is an object of the present invention to permit retention of the overall layout, and particularly the two chamber-per-branch detector arrangement, and still reduce the cross sensitivity.

DESCRIPTION OF THE INVENTION

It is an object of the present invention to improve the selectivity of two-beam, infrared gas analyzers.

It is a specific object of the present invention to improve infrared gas analyzers with regard to selectivity of the measurement, which analyzers include two modulated infrared beams traversing measuring and reference chambers or cells and reaching multiple detection cells or chambers filled with gas of the type to be detected and including a differential pressure-measuring chamber with capacitive pickup.

The analyzer, in accordance with the preferred embodiment of the present invention, is improved by not only providing front and rear detection chambers in the two branches as per the specific object, but the rear chamber means are configured for substantially complete absorption of radiation of the selected frequency; in addition, means are included for the nonselective attenuation of the effect of radiation on the rear chambers. The nonselective attenuation may be effective directly or indirectly. Direct attenuation is produced by filters, being interposed between the front- and rear-detection chambers; indirect attenuation is produced by diluting the rear detection chambers in a controlled manner as far as pressure is concerned. The rear chambers are preferably rather long, and conically shaped and provided with reflective inner surfaces.

It should be noted that a single-beam, nondispersive, infrared analyzer is known (German Pat. No. 1,017,385), having a front- and a rear-detection chamber and a movable diaphragm in between. This diaphragm is adjustable for fixing the zero point of the instrument for zero concentration. The position of the diaphragm during normal measurement, in relation to its previously adjusted zero point position, is used as an indication of the measured value. This patent deals also with cross sensitivity, but proposes to introduce definite amounts of the interfering components into the single measuring path. No relation is established between cross sensitivity and diaphragm.

The preferred embodiment of the invention, the objects and features of the invention, and further objects, features and advantages thereof, will be better understood from the following description taken in connection with the accompanying drawings.

Figure 1:
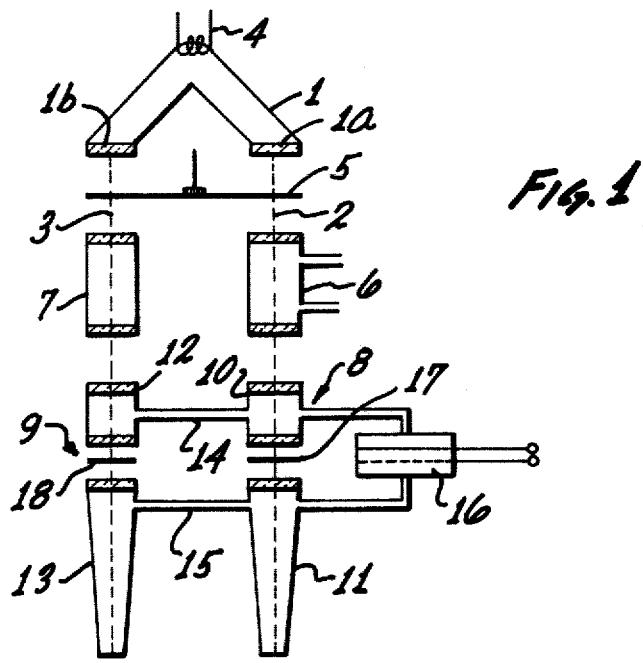
FIG. 1 is a schematic cross section through an infrared gas analyzer in accordance with the preferred embodiment of the invention, depicting the best mode of practicing same.

Proceeding now to the detailed description of the drawings, the figures show a source 4 for infrared radiation; and a path devider 1 is provided for obtaining two beams and branches 2 and 3, emerging from exit windows 1a and 1b in parallel relation to each other.

A motor-driven chopper wheel or disk 5 interrupts, alternatingly, the two beams and modulates them accordingly. A chamber or cell 6 for the measuring gas is traversed by beam 2. The chamber is a suitable vessel with aligned entrance and exit windows and inlet and outlet connections for continuous flow-through of gas to be analyzed. That gas contains the component to be detected and whose concentration is to be ascertained. The gas may be the exhaust fumes of an automobile, and the component to be detected may be a contaminant such as CO.

The other beam, 3, traverses a second cell or chamber 7 which contains a reference gas. Chamber 7 has likewise aligned entrance and exit windows; and usually, the dimensions of the chambers, 6 and 7, are the same, particularly in the direction of beam propagation. Also, for practical reasons, the various windows are of the same material and have the same thickness.

The two infrared beams are finally intercepted by detectors, 8 and 9 respectively, and constructed as two-level detectors. Detector 8 is comprised of two detection cells or chambers 10 and 11, traversed by beam 2 in that sequence. Analogously, detector 9 is comprised of two cells or chambers 12 and 13, traversed in that sequence by beam 3. All four chambers contain the gas component to be detected (e.g., contaminant CO).

The two front-end detection cells or chambers 12 and 10 are interconnected by a duct 14; and together, they are connected to one side of a differential pressure chamber 16, having two compartments which are separated from each other by a flexible membrane. This membrane constitutes one electrode of a pickup capacitor; any deflection of the membrane changes the capacitance. This change in capacitance represents the concentration of the component to be detected and is acquired electrically as an electrical signal.

The rear-end detection cells or chambers 11 and 13 are likewise interconnected by a duct 15; and together, they are connected to the other side of the differential chamber 16.

In the example shown in FIG. 1, radiation-attenuating disks, i.e. filters 17 and 18, are interposed between the respective front- and rear-detection chamber in the two radiation paths. The disks or filters attenuate the radiation in a nonselective manner as far as frequency is concerned. Thus, they have a broadband transmission-/attenuation range.

Figure 2:
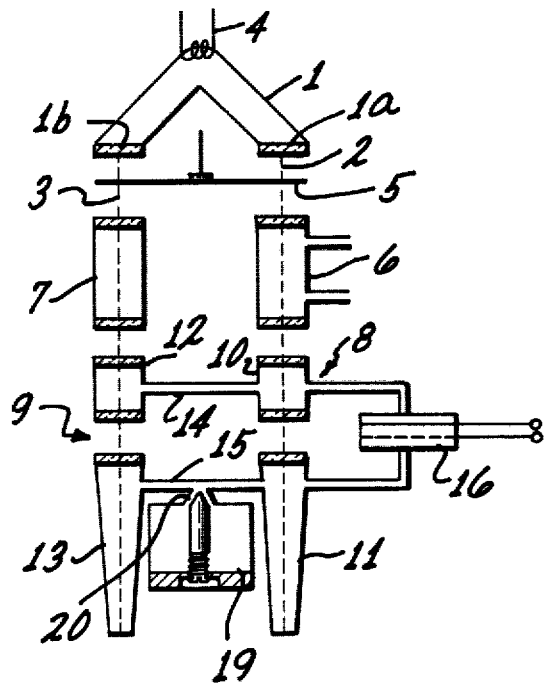
FIG. 2 is a modified example, still constituting the best mode of practicing the preferred embodiment of the invention.

In the example shown in FIG. 2, duct 15 is tapped to apply additional detection gas to the two chambers 11 and 13. Thus, an additional, or supplemental, chamber 19 is connected to duct 15 by means of an adjustable nozzle 20. Chamber 19 itself and its content is not being reached by the radiation of either branch; its function is to attenuate pressure fluctuations in the particular chamber system composed of cells 11 and 13 and one side of chamber 16 and chamber or cell 19.

In both examples, means have been introduced for attenuating the pressure variations in the rear-detection chambers. The optimum degree of attenuation, as far as selectivity enhancement is concerned, must be found through proper adjustment of these means. In the case of FIG. 2, this is obtained by varying the degree of opening and closing nozzle 20. The volume of chamber 19 must be sufficiently large in order to obtain a practicable range of adjustment. The solid material disks 17 and 18 provide nonselective absorption and/or reflection. By way of example, these filter disks may be the germanium wafers, silicon wafers, or fluorite wafers. Still alternatively, these disks may be transparent plates carrying thin coatings of metal or of the aforementioned materials.

In addition to the nonselective, i.e. wide-band, attenuation provided directly or indirectly by elements 17 through 20, it is necessary that the residual radiation, reaching rear chambers 11 and 13, is almost completely absorbed as far as the particular absorption line, lines, or bands, of the gas component of interest is concerned. If these frequency components are insufficiently absorbed in the detection chambers, the nonselective attenuation has little effect on the overall selectivity of the detection as such.

A variety of different features is available for ensuring full absorption of the radiation in cells or chambers 11 and 13. These features may well be used cumulatively, i.e., in combination. First of all, the rear chambers, 11 and 13, should be considerably longer than the front chambers 10 and 12; a suitable relation is a length for the rear chamber which is three-to-seven times the length of the front chambers. The internal wall surfaces of the rear chamber should be reflective; they may be made of gold, or are gold-plated. Moreover, the rear chambers should have a conical configuration, at least on the inside.

Analyzers of the type shown in the figures have been built; and particularly one of the analyzers of the variety shown in FIG. 1 has had the following construction features. The rear chambers 11 and 13 were four times as long as the front chambers 10 and 12. The rear chambers were conical, as shown, and had gold-plated inner walls. Partially reflective germanium wafers were used as attenuators 17 and 18.

Such an analyzer produced the following results. A measuring range of up to 100 ppm CO in diluted exhaust gas of automobiles and in the presence of 3% $CO_2$ and having a moisture content which is saturated at 20° C. did result in measuring errors of not more than 2 ppm CO at the upper-range end. Upon eliminating the attenuating disks, the performance deteriorated to errors of up to 12 ppm CO.

The invention is not limited to the embodiments described above; but all changes and modifications thereof, not constituting departures from the spirit and scope of the invention, are intended to be included.

We claim:

1. Nondispersive gas analyzer, including means for defining two infrared radiation beam branches, means disposed for modulating the beams of the branches; a measuring chamber and a reference chamber disposed respectively in the two branches; multichamber detection means including a differential pressure chamber with capacitive pickup for generating a measuring signal, and containing gas components of the type to be detected, the improvement in the detection means comprising:

front and rear detection chamber means disposed to be effective in each of the branches and connected to the differential pressure chamber, the rear detection chamber means being configured to absorb almost completely the radiation having particular frequency or frequencies of the said gas component to be detected; and means disposed to provide for nonfrequency-selective attenuation of the effect of radiation on the rear detection chamber means.

2. Analyzer as in claim 1, the rear detection chamber means being between three and seven times as long as the front detection chamber means, taken in direction of beam propagation through the chamber means.

3. Analyzer as in claim 1 or 2, the rear chamber means having reflective inner surfaces.

4. Analyzer as in claim 3, the inner surfaces being made of gold or being gold-plated.

5. Analyzer as in claim 1 or 2, the rear chamber means having a conical configuration.

6. Analyzer as in claim 1, wherein the rear chamber means are conically shaped and three to seven times as long as the front chamber means and having reflective surfaces.

7. Analyzer as in claim 1 or 6, the nonselective attenuation means being directly effective upon the radiation and including attenuating filter means disposed between the front and the rear detection chamber means.

8. Analyzer as in claim 7, the filter means being made of one of the following: germanium wafers, silicon wafers, or fluorite wafers.

9. Analyzer as in claim 1 or 6, wherein the attenuation means includes a chamber with said component gas and is connected via an adjustable element to the rear detection chamber means.

* * * * *